(12) United States Patent
Xie et al.

(10) Patent No.: US 10,149,657 B2
(45) Date of Patent: Dec. 11, 2018

(54) ON-LINE ENERGY COINCIDENCE METHOD AND SYSTEM FOR ALL-DIGITAL PET SYSTEM

(71) Applicant: RAYCAN TECHNOLOGY CO., LTD. (SU ZHOU), Suzhou New District, Suzhou, Jiangsu (CN)

(72) Inventors: Qingguo Xie, Jiangsu (CN); Xiaoke Wu, Jiangsu (CN); Jun Zhu, Jiangsu (CN); Ming Niu, Jiangsu (CN); Zhihao Hu, Jiangsu (CN); Luyao Wang, Jiangsu (CN)

(73) Assignee: Raycan Technology Co., Ltd. (Suzhou), Suzhou, Jiangsu (CN)

( * ) Notice: Subject to any disclaimer, the term of this patent is extended or adjusted under 35 U.S.C. 154(b) by 257 days.

(21) Appl. No.: 14/899,100

(22) PCT Filed: Nov. 14, 2013

(86) PCT No.: PCT/CN2013/087121
§ 371 (c)(1),
(2) Date: Dec. 16, 2015

(87) PCT Pub. No.: WO2015/010393
PCT Pub. Date: Jan. 29, 2015

(65) Prior Publication Data
US 2016/0324498 A1 Nov. 10, 2016

(30) Foreign Application Priority Data

Jul. 25, 2013 (CN) .......................... 2013 1 0315457

(51) Int. Cl.
*A61B 6/00* (2006.01)
*G01T 1/164* (2006.01)
(Continued)

(52) U.S. Cl.
CPC ............ *A61B 6/5205* (2013.01); *A61B 6/037* (2013.01); *A61B 6/4258* (2013.01);
(Continued)

(58) Field of Classification Search
CPC ....... A61B 6/4258; A61B 3/102; A61B 6/025; A61B 6/03; A61B 6/037; A61B 6/5235; G01T 1/2985
(Continued)

(56) References Cited

U.S. PATENT DOCUMENTS 8,452,064 B2 5/2013 Ross et al.
9,316,743 B2 * 4/2016 Rousso ................. G01T 1/1603
(Continued)

FOREIGN PATENT DOCUMENTS

CN 1910472 A 2/2007
CN 101268949 A 9/2008
(Continued)

OTHER PUBLICATIONS

Streun et al., The Data Acquisition System of a ClearPET Neuro—a Small Animal PET Scanner IEEE Transactions on Nuclear Science, vol. 53, No. 3, Jun. 2006.
(Continued)

*Primary Examiner* — Lam Nguyen
(74) *Attorney, Agent, or Firm* — Knobbe, Martens, Olson & Bear, LLP (57) ABSTRACT

An on-line energy coincidence method for an all-digital PET system, comprising: a detection module conducting information collection on a scintillation pulse, forming a single event data frame and sending it to an upper computer; the upper computer conducting two-bit position distribution statistics on an incident gamma photon event and conducting position spectrum partition; performing statistics on an energy distribution spectrum of each crystal bar, so as to acquire an energy correction value; the detection module uploading a crystal bar partition data table and an energy peak correction data table; starting information collection of on-line energy correction; when an event is coming, accord-
(Continued)

ing to a two-dimensional coordinate thereof, from the crystal partition table, searching for a crystal bar number corresponding thereto, and searching for an energy correction value from the energy correction table; and sending data passing the energy coincidence to the upper computer.

12 Claims, 3 Drawing Sheets

(51) Int. Cl.
*G01T 1/202* (2006.01)
*A61B 6/03* (2006.01)
*G01T 1/29* (2006.01)

(52) U.S. Cl.
CPC ............ *G01T 1/1647* (2013.01); *G01T 1/202* (2013.01); *G01T 1/2985* (2013.01)

(58) Field of Classification Search
USPC ............................................ 250/362, 363.04
See application file for complete search history.

(56) References Cited

U.S. PATENT DOCUMENTS

| | | | | |
|---|---|---|---|---|
| 2005/0145797 A1* | 7/2005 | Oaknin | ................ | A61B 6/4057 |
| | | | | 250/363.04 |
| 2008/0128626 A1* | 6/2008 | Rousso | .................. | A61B 5/415 |
| | | | | 250/362 |
| 2014/0270443 A1* | 9/2014 | Vija | ........................ | A61B 6/037 |
| | | | | 382/131 |
| 2016/0324498 A1* | 11/2016 | Xie | ........................ | G01T 1/1647 |

FOREIGN PATENT DOCUMENTS

| | | |
|---|---|---|
| CN | 101561507 A | 10/2009 |
| CN | 102262238 A | 11/2011 |
| CN | 102327125 A | 1/2012 |

OTHER PUBLICATIONS

Hegyesi, Ethernet Based Distributed Data Acquisition Systems for a Smal Animal PET IEEE Transactions on Nuclear Science Aug. 21, 2006.

\* cited by examiner

Figure 5 ional Application No. PCT/CN2013/087121, titled "ON-LINE ENERGY COINCIDENCE METHOD AND SYSTEM FOR ALL-DIGITAL PET SYSTEM", filed on Nov. 14, 2013, which claims priority to Chinese patent application No. 201310315457.7 titled "ON-LINE ENERGY COINCIDENCE METHOD AND SYSTEM FOR ALL-DIGITAL PET SYSTEM" and filed with the Chinese Patent Office on Jul. 25, 2013 which is incorporated herein by reference in its entirety.

ON-LINE ENERGY COINCIDENCE METHOD AND SYSTEM FOR ALL-DIGITAL PET SYSTEM

CROSS REFERENCE TO RELATED APPLICATION

This application is a national phase of International Application No. PCT/CN2013/087121, titled "ON-LINE ENERGY COINCIDENCE METHOD AND SYSTEM FOR ALL-DIGITAL PET SYSTEM", filed on Nov. 14, 2013, which claims priority to Chinese patent application No. 201310315457.7 titled "ON-LINE ENERGY COINCIDENCE METHOD AND SYSTEM FOR ALL-DIGITAL PET SYSTEM" and filed with the Chinese Patent Office on Jul. 25, 2013 which is incorporated herein by reference in its entirety.

FIELD

The present disclosure relates to the fields of high-energy radiation detection imaging and digital signal processing, and in particular to a method of online energy coincidence for an all-digital PET system.

BACKGROUND

The current main PET detector commonly employs the detecting structure in which array scintillation crystals are coupled to a photoelectric conversion device. After γ photons are incident on a crystal strip in the array of crystals, the Compton scattering or the photoelectric effect occurs, producing visible light signals. The photoelectric conversion device receives these optical signals and converts them into corresponding electrical signals. With the electrical signals, the coordinates (X, Y) of the incident position of the photon γ can be calculated. The number of the crystal strip where the γ photon event occurs is obtained based on the coordinates, to determine the Line of Response (also referred to as LOR) for the annihilation event.

However, in a practical PET system, before a pair of γ photons in opposite directions produced by the annihilation reach the detector, there would be a certain probability of occurrence of the Compton Effect in a biological tissue, resulting in the loss of energy and the change in the traveling direction of the γ photons. Finally the position where the γ photons are detected on the detector shifts. In this case, the detector may obtain an incorrect LOR for the annihilation event when using the actual incident position of the pair of γ photons. This is referred to as Scattering Events. To discriminate the scattering events, the usual practice is to employ energy coincidence, that is, setting up an energy window with the lowest and highest thresholds to determine each of the scintillation pulse events, and filtering out the event beyond the thresholds of the energy window.

In an ideal case, for the scintillation pulse event of each crystal strip of the array of the detector, energy statistics is made to obtain the same energy spectrum. However, in a practical implementation, since the gains of the photoelectric conversion devices are different and the resistor-weighted network used in the subsequent stage to determine the position has inconsistent energy responses regarding different positions, it is impossible to directly employ the same energy window to perform filtering. Instead, the data on crystal segmentation need to be taken into account, statistics for its energy spectrum information should be made, the energy of the scintillation pulse for each of the crystal strips is corrected to 511 keV, and then the energy window is used to perform energy coincidence.

There are several ways to achieve these processes, which are listed below.

The ClearPET detection modules developed by References document [1] produce single event frames. The single event frame must firstly be transmitted to multiple pretreatment personal computer (hereinafter simply referred to as PC) where crystal searching and energy correction operations are performed. The data suffering the energy coincidence then is transmitted to the main PC for the subsequent data process. However this method can not improve the effective data bandwidth of a single detection module. The highest counting rate that can be achieved by the single detection module is 478 kevents/s.

The miniPET developed by References document [2] and [3] uses a soft coincidence method. That is, after being formed by the detection module, the single event frame is transmitted to a host computer via Ethernet for coincidence detection. The crystal segmentation and energy correction operations are achieved via hardware according to this method. Accuracy, adaptability and scalability are poor. The counting rate that can be achieved by the single detection module is 90 kevents/s/detector.

The above methods can not meet the demand for the high counting rate required by the all-digital PET. Accordingly, for the above technical problems, there is a need for a full automatic method of online energy coincidence based on all-digital PET system to overcome the above disadvantages.

[1] Streun, M.; Brandenburg, G; Lame, H.; Parl, C.; Ziemons, K., "The data acquisition system of ClearPET neuro—a small animal PET scanner," Nuclear Science, IEEE Transactions on, vol. 53, no. 3, pp. 700, 703, June 2006.

[2] Hegyesi, G; Imrek, J.; Kalinka, G; Molnar, J.; Novak, D.; Végh, J.; Balkay, L.; Emri, M.; Kis, A.; Molnar, G; Tron, L.; Valastyan, I.; Bagamery, I.; Bukki, T.; Rozsa, S.; Szabo, Z.; Kerek, A., "Ethernet Based Distributed Data Acquisition System for a Small Animal PET," Nuclear Science, IEEE Transactions on, vol. 53, no. 4, pp. 2112, 2117, August 2006.

[3] Hegyesi, G; Imrek, J.; Kalinka, G; Molnar, J.; Novak, D.; Végh, J.; Balkay, L.; Emri, M.; Molnar, G; Tron, L.; Bagamery, I.; Bukki, T.; Rozsa, S.; Szabo, Z.; Kerek, A., "Development of an FPGA-based data acquisition module for small animal PET," Nuclear Science Symposium Conference Record, 2004 IEEE, vol. 5, no., pp. 2957, 2961, 16-22 Oct. 2004.

SUMMARY

In view of this, the purpose of the present disclosure is to provide a method and system of online energy coincidence for an all-digital PET system, achieving a full automatic and rapid online energy coincidence, to a large extent filtering out the useless data in transmission medium, and achieving a higher effective counting rate without affecting performance of the system.

To achieve the above purpose, the present disclosure provides the following technical solutions.

A method of online energy coincidence for an all-digital PET system is provided, wherein the method includes following steps:

S1: a detection module collecting information of scintillation pulses generated by incident γ photons, forming a data frame of a single event and transmitting the data frame to a host computer;

S2: the host computer performing two-dimensional position distribution statistics on the incident γ photons, acquiring a two-dimensional position spectrum of the incident γ photons, performing segmentation of the position spectrum to confine a region for each crystal strip, and forming a crystal segmentation table;

S3: after the segmentation, making statistics for an energy distribution spectrum of the scintillation pulses contained in each of the crystal strips, obtaining an energy value, as an energy correction value of a corresponding crystal strip, that actually corresponds to a 511 keV energy peak for each of the energy distribution spectrums by searching for a point at which count of each of the energy spectrums is the highest, to form an energy correction table, by the host computer;

S4: transmitting the crystal segmentation table and the energy correction table from the host computer to a storage unit of the detection module;

S5: collecting information of online energy correction by the detection module according to the crystal segmentation table and the energy correction table;

S6: when an event occurs, searching for the number of a corresponding crystal strip from the crystal segmentation table in accordance with a two-dimensional coordinate of the event, and searching for an energy correction value from the energy correction table in accordance with the number of the corresponding crystal strip; and S7: calculating a true energy value of the event in accordance with the searched energy correction value; reserving the event if the true energy value of the event is within an energy window; filtering out the event if the true energy value of the event is not within the energy window; and transmitting data of the reserved event to the host computer finally.

Preferably, in the method of online energy coincidence for the all-digital PET system, the information of scintillation pulses collected in Step S1 comprises time, energy and position information, the energy information is acquired by way of a Analog-Digital converter (hereinafter simply referred to as ADC), Multi-voltage Threshold (hereinafter simply referred to as MVT) or charge integration, and the position information is acquired by way of a resistor-weighted network method or a detector pixel one-to-one readout method.

Preferably, in the method of online energy coincidence for the all-digital PET system, performing segmentation of the position spectrum for each of the crystal strips on the collected data in Step S2 comprises using a Neural Network algorithm or a Dimensionality Reduction algorithm or a Watershed algorithm.

Preferably, in the method of online energy coincidence for the all-digital PET system, in Step S4, data is transmitted between the detection module and the host computer via fiber optic, Ethernet, USB, a bus, Bluetooth or a new wireless network data communication technology.

Preferably, in the method of online energy coincidence for the all-digital PET system, calculating the true energy value of the event in Step S7 comprises dividing an energy value of the event by the searched energy correction value, and then multiplied by 511 keV.

A system of online energy coincidence for an all-digital PET system is provided, wherein the system of online energy coincidence includes:

a scintillation pulse information acquiring module, configured to sample and process scintillation pulses and acquire energy, time and position information of the scintillation pulse;

an energy coincidence module, configured to correct energy values of the scintillation pulses and make a energy coincidence determination according to an energy window; and a crystal segmentation and energy spectrum peak-searching module, configured to determine a crystal segmentation table and an energy correction table.

Preferably, in the system of online energy coincidence for the all-digital PET system, the scintillation pulse information extracting module may include an energy acquiring module, a time acquiring module and a position acquiring module, wherein the energy acquiring module is configured to sample the scintillation pulses in time domain and acquire the energy values of the scintillation pulses;

the time acquiring module is configured to sample the scintillation pulses in voltage domain and acquire the time information of the scintillation pulses; and the position acquiring module is configured to acquire tow-dimensional position information of positions where the scintillation pulses are incident.

Preferably, in the system of online energy coincidence for the all-digital PET system, the energy values of the scintillation pulses are acquired by way of digital integration, or an integrating circuit, or MVT.

Preferably, in the system of online energy coincidence for the all-digital PET system, the time information of the scintillation pulses is acquired by a voltage comparator and a time-to-digital converter, or a high-speed ADC or analog or digital constant fraction discrimination, or a Leading Edge method.

Preferably, in the system of online energy coincidence for the all-digital PET system, the two-dimensional position information is acquired by calculating a ratio of a X axis component and a Y axis component of each of four angle signals generated by a front detector, or by reading pixel units of the detector one by one, or by employing light distribution information.

Preferably, in the system of online energy coincidence for the all-digital PET system, the energy coincidence module comprises the crystal segmentation table, the energy correction table, an energy correction module and an energy determination module, wherein the crystal segmentation table is configured to store data that maps X, Y two-dimensional coordinates to the numbers of crystal strips;

the energy correction table is configured to store data that maps the numbers of the crystal strips to energy correction values;

the energy correction module is configured to correct an original energy value of a data frame according to the energy correction values; and the energy determination module is configured to determine whether to filter out the data frame according to the corrected energy value of the data frame and the energy window.

Preferably, in the system of online energy coincidence for the all-digital PET system, the crystal segmentation and energy spectrum peak-searching module comprises a crystal segmentation module, an energy spectrum peak-searching module and an online energy correction data transmission module, wherein the crystal segmentation module is configured to perform position spectrum segmentation on pre-collected data to confine regions for crystal strips;

the energy spectrum peak-searching module is configured to make statistics on data of each of the crystal strips, and obtain an energy value, as an energy correction value of a corresponding crystal strip, that corresponds to a 511 keV energy peak for each of energy distribution spectrums by searching for a point at which count of each of the energy spectrums is the highest; and the online energy correction data transmission module is configured to transmit the crystal segmentation table and the energy correction table to an energy determination module.

Preferably, in the system of online energy coincidence for the all-digital PET system, the position spectrum segmentation is performed on the pre-collected data by a Neural Network algorithm, a Dimensionality Reduction algorithm or a Watershed algorithm.

As can be seen from the above technical solutions, based on all-digital soft coincidence PET system, the present disclosure has achieved a full automatic and rapid online energy coincidence. It not only meets the requirements of full automatic and rapid correction of variable-structure PET, but also to a large extent filters out useless data in transmission medium, improving the effective data bandwidth. The high complexity but accurate crystal segmentation algorithm is achieved easily in the host computer by using a soft coincidence PET information collection system, and achieving the exact segmentation for the crystal and determination of the energy correction coefficient. Crystal strip lookup table and energy correction data are sent back to the detection module, and hence the useless energy data out of the energy window is effectively removed. A higher effective counting rate is achieved with affecting performance of the system.

Compared with the conventional art, the beneficial effects of the present disclosure are as follows.

(1) A full automatic and rapid correction is achieved to meet the requirements for variable-structure PET and to allow the system to keep at the optimum working condition for a long term;

(2) The effective counting rate of each of the detection units is improved by energy coincidence, and the limit of the transmission bandwidth is reduced, so that the PET system is applied to the case of a high counting rate.

BRIEF DESCRIPTION OF THE DRAWINGS

In order to illustrate technical solutions in embodiments of the present disclosure or the conventional technology more clearly, hereinafter drawings to be used in the description of the embodiments or the conventional technology will be introduced simply. Apparently, the drawings described below only describe some embodiments of the present disclosure, and other embodiments and drawings may be obtained based on the embodiments described by these drawings by those skilled in the art.

FIG. 3(a) is the schematic view without employing the method of online energy coincidence for the all-digital PET system according to the disclosure, and FIG. 3(b) is the schematic view with employing the method of online energy coincidence for the all-digital PET system according to the disclosure;

DETAILED DESCRIPTION

Compared to the traditional PET, an all-digital PET system is flexible, scalable, and easy to be corrected. Because the system is all built by employing a general digital logic devices, it may perform easily and quickly presetting, monitoring and correction for all the variable parameters of the information collection system, allowing the system performance to maintain at the optimum condition.

Scintillation pulses may be directly digitized by employing MVT and other methods. The information of the scintillation pulse is acquired more accurately. Meanwhile the dead time for front information collection becomes very short since shaping and filtering are not required, accordingly achieving a high counting rate. This may effectively enhance the signal to noise ratio of the image, making dynamic imaging, short half-life radionuclide and other applications possible.

Soft coincidence of the PET system means: each of the detection modules separately handles the event of the scintillation pulse, and acquires time, energy, and position information, forms data frames that contains all the information of the single event, and transmits the data frames to the host computer to perform coincidence processing to extract the true event. The information of the scintillation pulse event can be completely obtained and be transmitted to the host computer, accordingly information required by a more excellent scheme may be extracted and the system performance may also be improved by the development of the consumer electronics and computer industries. The soft coincidence system requires the detection module to transmit the collected data frames of the single event to the host computer completely, which greatly enhances the amount of transmitted data.

Accordingly, the PET system that is built based on the above features has a very high demand for the effective transmission bandwidth of the detection module.

The imaging principle of the PET system requires coincidence detection to a pair of γ photons in opposite directions which are produced every time the annihilation event occurs in the human body, and each photon has the energy of 511 keV. However, in the practical process, since γ photons may possibly suffer from a Compton scattering due to tissues in the human body, its direction of travel may be changed. Thus, a wrong line of response is obtained via the γ photon. To filter out such an event, considering the reduction of the energy of the scattering γ photon, the method of the energy coincidence may be used to distinguish this kind of γ photon from those without suffering scattering.

Ideally, the same energy spectrum should be obtained by calculating the energy value of the incident scintillation pulse event, for each of the positions in the detector. However, in the practical implementation, since the gains of photoelectric conversion devices are different and the resistors-weighted network used in the subsequent stage for determining the position has inconsistent energy responses regarding different positions of the detection array, it is impossible to directly employ the same energy window to perform filtering. Instead, the data on crystal segmentation need to be taken into account, statistics for information on energy spectrum of each of the crystal strips should be made, and the energy correction coefficient need to be obtained. After the energy of the scintillation pulse for each of the crystal strips is corrected to 511 keV, the energy window is used to perform energy coincidence determination.

Based on the above, the present disclosure provides a method of online energy coincidence for an all-digital PET system. The method has achieved a full automatic and rapid online energy coincidence. It not only meets the requirements of full automatic and rapid correction of variable-structure PET, but also to a large extent filters out the useless data in transmission medium, improving the effective data bandwidth. The high complexity and accurate crystal segmentation algorithm is achieved easily in the host computer by using a soft coincidence PET information collection system, achieving the accurate segmentation for the crystal and determination of the energy correction coefficient. Crystal strip lookup table and energy correction data are sent back to the detection module, and hence the useless data out of the energy window is effectively removed. A higher effective counting rate is achieved without affecting performance of the system.

The technical solution according to the embodiments of the present disclosure will be described in details as follows in conjunction with the accompany drawings in the embodiments of the present disclosure. It is obvious that the described embodiments are only a part of the embodiments according to the present disclosure. All the other embodiments obtained by those skilled in the art based on the embodiments in the present disclosure without any creative work belong to the scope of the present disclosure.

Figure 1:
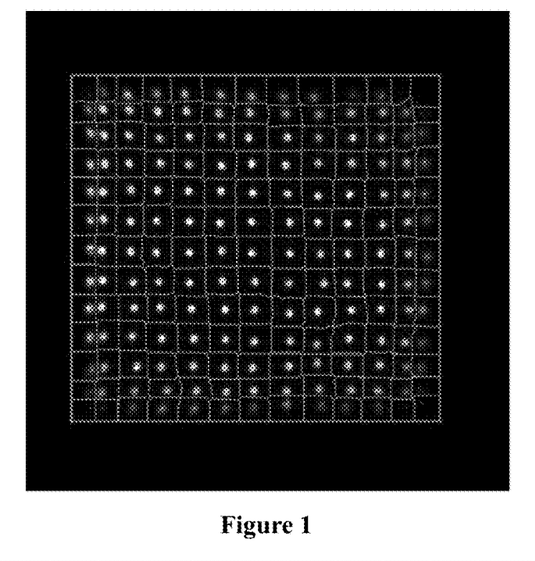
FIG. 1 is a diagram showing the result that is obtained by segmenting the position spectrum for the crystal at the host computer in the method of online energy coincidence for the all-digital PET system according to the present disclosure.
Figure 2:
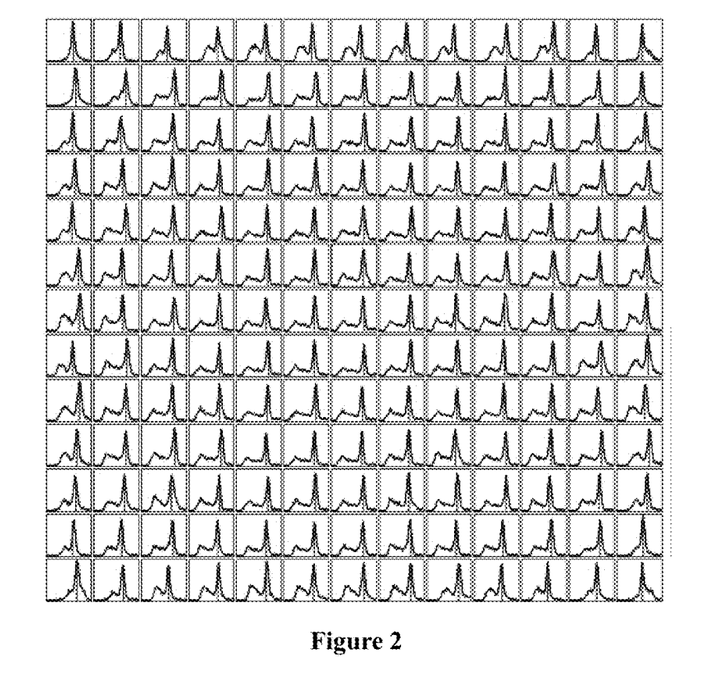
FIG. 2 is a plot of the energy spectrum data that is obtained by making statistics for the energy value of the event that is contained in each of the crystal strips in the method of online energy coincidence for the all-digital PET system according to the present disclosure.

As shown in FIGS. 1 and 2, the method of online energy coincidence for the all-digital PET system disclosed includes the following steps:

S1: collecting information of scintillation pulses generated by incident γ photons, forming a data frame of a single event and transmitting the data frame to a host computer, by a detection module;

S2: performing two-dimensional position distribution statistics on the incident γ photons, acquiring a two-dimensional position spectrum of the incident γ photons, performing segmentation for the position spectrum to confine a region for each of crystal strips, and forming a crystal segmentation table, by the host computer, as shown in FIG. 1;

S3: after the segmentation, making statistics for energy distribution spectrums of the scintillation pulse contained in each of the crystal strips, acquiring the energy value that actually corresponds to a 511 keV energy peak for each of the energy distribution spectrums by searching for the point at which the count of each of the energy spectrums is the highest, and using this value as a energy correction value of a corresponding crystal strip to form an energy correction table, by the host computer, as shown in FIG. 2;

S4: transmitting the crystal segmentation table and the energy correction table from the host computer to a storage unit of the detection module;

S5: collecting information of the online energy correction by the detection module according to the crystal segmentation table and the energy correction table;

S6: when an event occurs, searching for the number of a corresponding crystal strip from the crystal segmentation table in accordance with a two-dimensional coordinate of the event, and searching for an energy correction value from the energy correction table in accordance with the number of the crystal strip; and S7: calculating a true energy value of the event in accordance with the energy correction value; reserving the event if the true energy value of the event is within an energy window; filtering out the event if the true energy value of the event is not within the energy window; and transmitting data of the reserved event to the host computer.

Specifically, the information of scintillation pulses collected in Step S1 includes time, energy and position information. Specifically, the energy information is acquired by way of ADC, or MVT, or a charge integration method. The position information is acquired by way of the method of resistor-weighted network, or the method of detector pixel one-to-one readout. The ways would not be enumerated here; any alternative ways are within the protection scope of the present disclosure.

Specifically, the algorithm for performing segmentation of the position spectrum of the crystal strips on the collected data in Step S2 includes a Neural Network algorithm, or a Dimensionality Reduction algorithm or a Watershed algorithm. The algorithms would not be enumerated here, and any alternative algorithms are within the protection scope of the present disclosure.

Specifically, in the Step S4, data may be transmitted between the detection module and the host computer via fiber optic, Ethernet, USB, a bus, Bluetooth, or a new wireless network data communication technology (zigbee) or other alternative media, which may not be enumerated here, any alternative media are within the protection scope of the present disclosure.

Specifically, in the Step S4, the storage medium of the detection module for storing the crystal strip lookup table and the energy correction table includes off-chip RAM, on-chip RAM, or off-chip FLASH.

Specifically, in the Step S4, the storage format in which the detection module stores the crystal strip lookup table and the energy correction table includes direct lookup by using the X, Y energy values of the event as a two-dimensional address, or one-dimensional lookup by organizing the table to a format of a run length code.

Specifically, in Step S7, the true energy value of the event is obtained by dividing energy value of the event by the energy correction value, and then multiplied by 511 keV. The energy window usually has a lower limit of 350 keV, and an upper limit of 650 keV.

Figure 3:
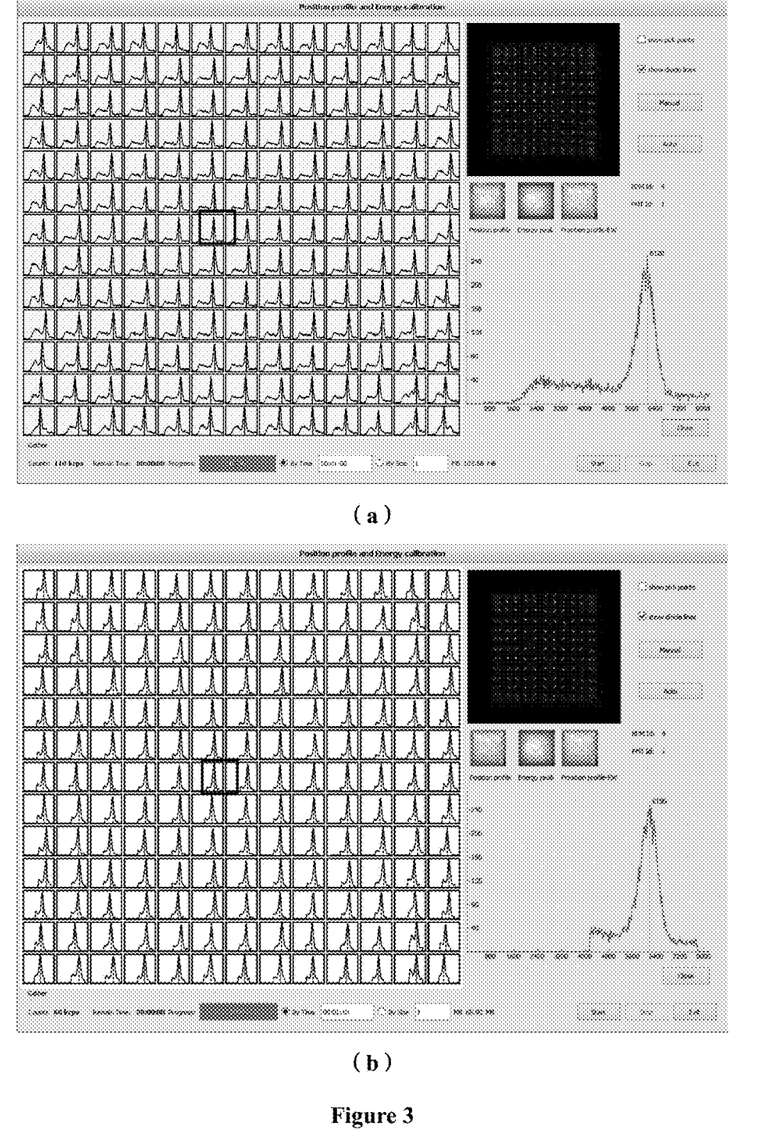
FIG. 3 is a comparison chart for the position spectrum and the energy spectrum of each of the crystal strips, which are obtained by collecting information before and after employing the method of online energy coincidence for the all-digital PET system according to the disclosure. Specifically.

As shown in FIG. 3, FIG. 3 is a comparison chart for the position spectrum and the energy spectrum of each of the crystal strips, which are obtained by collecting information before and after employing the method of online energy coincidence for the all-digital PET system according to the disclosure. Specifically, FIG. 3(a) is the schematic view without employing the method of online energy coincidence for the all-digital PET system according to the disclosure, and FIG. 3(b) is the schematic view with employing the method of online energy coincidence for the all-digital PET system according to the disclosure. From FIG. 3 it can be seen:

1. The information of the counting rate of the detection module is provided in the Counts column at the lower right corner of the diagram. It can be seen from FIGS. 3(a) and 3(b) that the counting rate is 110 kcps without employing online energy coincidence and the counting rate is 60 kcps with online energy coincidence. That is, this method greatly reduces the counting rate, thereby reducing the load of data transmission bandwidth.

2. By the comparison of the energy spectrum (13*13 small figure on the left) of each of the crystal strips in the two figures, it can be seen that the data whose energy spectrum falls outside the energy window is filtered out, and the effective data inside the energy window is lossless. The lower right corner gives an enlarged view of the energy spectrum of the crystal strip selected by the black box on the left side, which may show the effect of the online energy coincidence more clearly.

3. The position spectrum is given at the top right corner. Compared the position spectrums before and after the online energy coincidence, there is no change in the position spectrums. It can be seen that this method would no affect acquisition for the position information.

Figure 4:
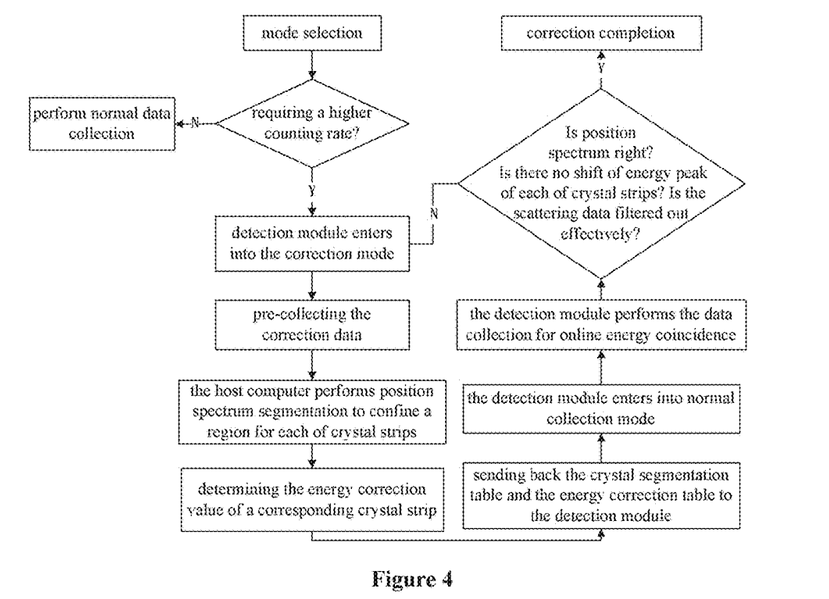
FIG. 4 is a flowchart of the method of online energy coincidence for the all-digital PET system according to the disclosure.

As shown in FIG. 4, FIG. 4 is the process flowchart of the method of online energy coincidence for the all-digital PET system according to the disclosure. The processes are described in the following. A mode is selected at first. Normal information collection is performed if there is no demand for a high computation rate. If there is a demand for high computation rate, the detection module is set into the correction mode, and the pre-collection for the corrected data is performed on the scintillation pulses produced by the incident γ photons to form the data frame of a single event. Then the data frame is transmitted to the host computer. The host computer performs two-dimensional position distribution statistics on the incident γ photons, acquires the two-dimensional position spectrum of the incident γ photons, and then segments the position spectrum. After the segmentation, the host computer make statistics for the energy distribution spectrum of the scintillation pulses for each of the crystal strips, and acquires the energy value corresponding to 511 keV energy peak for each of the energy distribution spectrums by searching for the point at which the count of the energy spectrum is the highest, and uses this value as the energy correction value of the corresponding crystal strip. Then the crystal segmentation table and the energy correction table are transmitted from the host computer to the storage unit of the detection module. The detection module loads the crystal segmentation table and the energy correction table, and enters the normal collection mode, that is, beginning collecting the information on the online energy correction. The true energy value of the event is calculated in accordance with the energy correction value: if the true energy value of the event is within the energy window, the event is reserved; if the true energy value of the event is not within the energy window, the event is filtered out; then the data of the reserved event is transmitted to the host computer. These steps are repeated until the position spectrum is right and the energy peak of each of the crystal strips has no shift and the scattering data are effectively filtered out. At this time, the correction is completed. Otherwise, the detection module enters the correction mode again and begins the next cycle.

Figure 5:
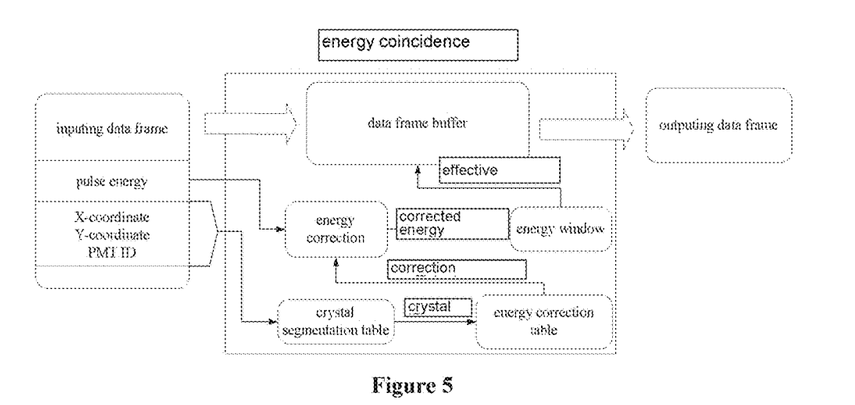
FIG. 5 illustrates the hardware structure for implementing the online energy coincidence process according to the method of online energy coincidence for the all-digital PET system according to the disclosure.

As shown in FIG. 5, FIG. 5 illustrates the hardware structure for implementing the online energy coincidence process according to the method of online energy coincidence for the all-digital PET system according to the disclosure. The process of the online energy coincidence as described in FIG. 5 is as follows. When any γ photon is incident on the detector, the front detection module may acquire the energy value and X, Y two-dimensional position coordinate and PMT ID information of the γ photon, and so on, and these information may constitute a data frame which is input to the energy coincidence module. The energy coincidence module searches for the ID of the crystal strip corresponding to the event in the crystal lookup table according to X, Y two-dimensional position coordinate and PMT ID, and acquires the corresponding correction coefficient in the energy correction table according to the ID of the crystal strip. The energy value of the data frame is corrected with the correction coefficient, and the corrected energy value is determined according to the energy window. The data frame is transmitted to the processing module in the subsequent stage if the energy value is within the energy window; otherwise, the data frame is discarded.

The present disclosure further provided a system of online energy coincidence for an all-digital PET system. The system of online energy coincidence includes the followings:

a scintillation pulse information extracting module, configured to sample and process scintillation pulses to acquire energy, time and position information of the scintillation pulse;

an energy coincidence module, configured to correct an energy value of the scintillation pulse, and to make a energy coincidence determination according to an energy window; and a crystal segmentation and energy spectrum peak-searching module, configured to determine a crystal segmentation table and a energy correction table.

Specifically, the scintillation pulse information extracting module includes an energy acquiring module, a time acquiring module and a position acquiring module.

Specifically, the energy acquiring module is configured to sample the scintillation pulse in time domain, and to acquire an energy value of the scintillation pulse by way of digital integration; or to directly acquire the energy value of the scintillation pulse by using an integrating circuit; or to acquire the energy value of the scintillation pulse by MVT. There may be various ways, which are not enumerated herein, and any alternative ways are within the protection scope of the present disclosure.

The energy acquiring module is configured to sample the scintillation pulse in time domain, and to acquire an energy value of the scintillation pulse by way of digital integration; or to directly acquire the energy value of the scintillation pulse by using an integrating circuit; or to acquire the energy value of the scintillation pulse by MVT. There may be various ways, which are not enumerated herein; any alternative ways are within the protection scope of the present disclosure.

The time acquiring module is configured to sample the scintillation pulse in voltage domain, and to acquire the time information of the scintillation pulse by employing a voltage comparator and a time-to-digital converter; or to acquire the time information of the scintillation pulse via a high-speed ADC; or to acquire the time information of the scintillation pulse via analog or digital constant fraction discrimination (Constant Fraction Discrimination, referred to as CFD); or to acquire the time information of the scintillation pulse by employing the Leading Edge method. Since there is no proper Chinese translation for the Leading Edge method in the industry and the skilled in the art are accustomed to this expression, the English expression is reserved in the claims of the present disclosure so as to express exactly the method protected in the claims in the present disclosure. There may be various ways, which are not enumerated herein; any alternative ways are within the protection scope of the present disclosure.

Specifically, the energy coincidence module includes the crystal segmentation table, the energy correction table, an energy correction module and an energy determination module.

Specifically, the crystal segmentation table is configured to store data that maps the X, Y two-dimensional coordinate to the number of the crystal strip;

the energy correction table is configured to store data that maps the number of the crystal strip to the corrected value of the energy;

the energy correction module is configured to correct the original energy value of the data frames according to the corrected value of the energy; and the energy determination module is configured to determine whether to filter out the data frame according to the corrected energy value and the energy window.

Specifically, the crystal segmentation and energy spectrum peak-searching module includes a crystal segmentation module, an energy spectrum peak-searching module and an online energy correction data transmission module.

Specifically, the crystal segmentation module is configured to perform position spectrum segmentation on the pre-collected data to confine a region of the crystal strip.

The energy spectrum peak-searching module is configured to make statistics on the data of each of the crystal strips, and to acquire the energy value corresponding to the energy peak of 511 keV for each of the energy distribution spectrums by searching for the point at which the count of each of the energy spectrums is the highest, and to use this value as the energy correction value of the corresponding crystal strip.

The online energy correction data transmission module is configured to transmit the crystal segmentation table and the energy correction table to the energy determination module.

Specifically, the algorithm for performing the position spectrum segmentation on the pre-collected data includes a Neural Network algorithm, a Dimensionality Reduction algorithm or a Watershed algorithm.

The method according to all-digital soft coincidence PET system, firstly performs pre-collection to get the data of position spectrum without any screening process, and may segment accurately the data of the position spectrum and obtain the energy spectrum of the event contained in each of the crystal strips in software, thus obtaining accurate energy correction value. It has realized a full automatic and fast online energy coincidence. It not only meets the requirements of full automatic and rapid correction of variable-structure PET, but also to a large extent filters out unwanted data in transmission medium, improving the effective data bandwidth. The high complexity but accurate crystal segmentation algorithm is achieved easily in the host computer by using a soft coincidence PET information collection system, achieving the exact segmentation of the crystal and determination of the energy correction coefficient. Crystal strip lookup table and energy correction data are sent back detection module. The useless data out of the energy window are effectively removed according to the information. A higher effective counting rate is achieved with affecting performance of the system.

In the present disclosure, the energy coincidence is performed at the detection module stage, which significantly reduced the percentage of useless data in the data that is transmitted from the detection module to the host computer and provides a platform to obtain high and affective counting rate required by the soft coincidence and full digitalization.

For those skilled in the art, the present disclosure is clearly not limited to the details of the above-described exemplary embodiments, and without departing from the spirit or essential characteristics of the present disclosure; the present disclosure can be achieved in other specific forms. Therefore, no matter from what point of view, the embodiments should be considered to be exemplary but not limiting. The scope of the present disclosure is defined by the appended claims rather than the above-described description; therefore, all changes falling within the meaning and range of an equivalent of the claims are intended to be included within the present disclosure. Any reference numeral in the claims should not be seen to restrict the referred claims.

Further, it should be understood that, although the present specification is described according to the embodiments, not every embodiment contains only a separate technical solution, this narrative mode is merely for the sake of clarity. Those skilled in the art should consider the specification as a whole; the technical solutions of each embodiment may be appropriately combined to form other embodiments which those skilled in the art can appreciate.

What is claimed is:

1. A method of online energy coincidence for an all-digital PET system, wherein the method comprises:
   S1: collecting information of scintillation pulses generated by incident γ photons, forming a data frame of a single event and transmitting the data frame to a host computer, by a detector module, wherein: the detector module comprises a plurality of crystal strips, each of the plurality of crystal strips is identified by a number of the crystal strip, wherein the information of scintillation pulses comprises time, energy and position information, and wherein the single event refers to hitting of an incident γ photon to one of the plurality of the crystal strips;
   S2: performing two-dimensional position distribution statistics on the incident γ photons to acquire X, Y two-dimensional coordinates of each of the incident γ photons which form a two-dimensional position spectrum of the incident γ photons, performing segmentation of the position spectrum to map X, Y two-dimensional coordinates to the numbers of the plurality of crystal strips, and forming a crystal segmentation table, by the host computer;
   S3: after the segmentation, calculating the energy information included in the data frame of the single event to acquire an energy distribution spectrum of the scintillation pulses contained in each of the crystal strips, obtaining an energy value, as an energy correction value of a corresponding crystal strip, that actually corresponds to a 511 keV energy peak for each of the energy distribution spectrums by searching for a point at which count of each of the energy spectrums is the highest, to form an energy correction table, by the host computer;
   S4: transmitting the crystal segmentation table and the energy correction table from the host computer to a storage unit of the detector module;
   S5: collecting information of online energy correction by the detector module according to the crystal segmentation table and the energy correction table;

S6: when a single event occurs, searching the crystal segmentation table to obtain the number of a corresponding crystal strip which maps to the single event in accordance with a two-dimensional coordinate of the single event, and searching the energy correction table to obtain an energy correction value in accordance with the number of the corresponding crystal strip, by the detector module, wherein the crystal segmentation table and the energy correction table are in a format of lookup table; and S7: calculating a true energy value of the single event in accordance with a searched energy correction value, reserving the single event if the true energy value of the single event is within an energy window, filtering out the single event if the true energy value of the single event is not within the energy window, and transmitting data of the reserved single event to the host computer, by the detector module.

2. The method of online energy coincidence for the all-digital PET system according to claim 1, wherein the information of scintillation pulses collected in Step S1 comprises time, energy and position information, wherein the energy information is acquired by way of a Analog-Digital converter, Multi-voltage Threshold or charge integration, and the position information is acquired by way of a resistor-weighted network method or a detector pixel one-to-one readout method.

3. The method of online energy coincidence for the all-digital PET system according to claim 1, wherein performing segmentation of the position spectrum for each of the crystal strips on the collected data in Step S2 comprises using a Neural Network algorithm or a Dimensionality Reduction algorithm or a Watershed algorithm.

4. The method of online energy coincidence for the all-digital PET system according to claim 1, wherein, in Step S4, data is transmitted between the detector module and the host computer via fiber optic, Ethernet, USB, a bus, Bluetooth or a new wireless network data communication technology.

5. The method of online energy coincidence for the all-digital PET system according to claim 1, wherein, calculating the true energy value of the event in Step S7 comprises dividing an energy value of the event by the searched energy correction value, and then multiplied by 511 keV.

6. A system of online energy coincidence for an all-digital PET system, wherein the system of online energy coincidence comprises:
a scintillation pulse information extracting module, configured to sample and process scintillation pulses and acquire energy, time and position information of the scintillation pulses;
an energy coincidence module, configured to correct energy values of the scintillation pulses and make energy coincidence determination according to an energy window; and
a crystal segmentation and energy spectrum peak-searching module, configured to determine a crystal segmentation table and an energy correction table,
wherein the scintillation pulse information extracting module comprises an energy acquiring module, a time acquiring module and a position acquiring module, wherein
the energy acquiring module is configured to sample the scintillation pulses in time domain, and acquire the energy values of the scintillation pulses by way of an integrating circuit;
the time acquiring module is configured to sample the scintillation pulses in voltage domain, and acquire the time information of the scintillation pulses by any one of: a voltage comparator and a time-to-digital converter; a high-speed Analog-to-Digital converter; and analog or digital constant fraction discrimination; and
the position acquiring module is configured to acquire two-dimensional position information of positions by calculating a ratio of a X axis component and a Y axis component of each of four angle signals generated by a front detector, or by reading pixel units of a detector one by one, where the scintillation pulses are incident;
wherein the energy coincidence module comprises the crystal segmentation table, the energy correction table, an energy correction module and an energy determination module, wherein
the crystal segmentation table is configured to store data that maps X, Y two-dimensional coordinates to the numbers of crystal strips;
the energy correction table is configured to store data that maps the numbers of the crystal strips to energy correction values;
the energy correction module is configured to correct an original energy value of a data frame according to the energy correction values; and
the energy determination module is configured to determine whether to filter out the data frame according to the corrected energy value of the data frame and the energy window.

7. The system of online energy coincidence for the all-digital PET system according to claim 6, wherein the scintillation pulse information extracting module comprises an energy acquiring module, a time acquiring module and a position acquiring module; wherein
the energy acquiring module is configured to sample the scintillation pulses in time domain and acquire the energy values of the scintillation pulses;
the time acquiring module is configured to sample the scintillation pulses in voltage domain and acquire the time information of the scintillation pulses; and
the position acquiring module is configured to acquire two-dimensional position information of positions where the scintillation pulses are incident.

8. The system of online energy coincidence for the all-digital PET system according to claim 7, wherein the energy values of the scintillation pulses are acquired by way of digital integration, or an integrating circuit, or Multi-Voltage Threshold.

9. The system of online energy coincidence for the all-digital PET system according to claim 7, wherein the time information of the scintillation pulses is acquired by a voltage comparator and a time-to-digital converter, or a high-speed Analog-to-Digital converter, or analog or digital constant fraction discrimination, or a Leading Edge method.

10. The system of online energy coincidence for the all-digital PET system according to claim 7, wherein the two-dimensional position information is acquired by calculating a ratio of a X axis component and a Y axis component of each of four angle signals generated by a front detector; or by reading pixel units of the detector one by one; or by employing light distribution information.

11. The system of online energy coincidence for the all-digital PET system according to claim 6, Wherein the crystal segmentation and energy spectrum peak-searching module comprises a crystal segmentation module, an energy spectrum peak-searching module and an online energy correction data transmission module, wherein the crystal segmentation module is configured to perform position spectrum segmentation on pre-collected data to confine regions for crystal strips;

the energy spectrum peak-searching module is configured to make statistics on data of each of the crystal snips, and obtain an energy value, as an energy correction value of a corresponding crystal strip, that corresponds to a 511 keV energy peak for each of energy distribution spectrums by searching for a point at which count of each of the energy spectrums is the highest; and the online energy correction data transmission module is configured to transmit the crystal segmentation table and the energy correction table to an energy determination module.

12. The system of online energy coincidence for the all-digital PET system according to claim 11, wherein the position spectrum segmentation is performed on the pre-collected data by a Neural Network algorithm, a Dimensionality Reduction algorithm or a Watershed algorithm.

* * * * *